United States Patent [19]

Hartwig

[11] 4,197,844
[45] Apr. 15, 1980

[54] MONITOR DEVICE FOR A VENTILATION UNIT

[75] Inventor: Hans-Joachim Hartwig, Lübeck, Fed. Rep. of Germany

[73] Assignee: Drägerwerk Aktiengesellschaft, Fed. Rep. of Germany

[21] Appl. No.: 870,832

[22] Filed: Jan. 19, 1978

[30] Foreign Application Priority Data

Jan. 20, 1977 [DE] Fed. Rep. of Germany ....... 2702125

[51] Int. Cl.² ............................................ A61M 16/00
[52] U.S. Cl. ............................................... 128/205.23
[58] Field of Search ......................... 128/145.5–145.8, 128/DIG. 29, 142.4; 116/112, 70, 114 PV, 65; 137/557

[56] References Cited

U.S. PATENT DOCUMENTS 3,223,068  12/1965  Van Winkle ........................... 116/65
3,664,370  5/1972  Warnow ........................ 128/145.8 X

FOREIGN PATENT DOCUMENTS 2405555  8/1975  Fed. Rep. of Germany ........ 128/145.8
1398752  6/1975  United Kingdom ............ 128/DIG. 29

*Primary Examiner*—Henry J. Recla
*Attorney, Agent, or Firm*—McGlew and Tuttle

[57] ABSTRACT

A monitoring device for monitoring the breathing air pressure in a breathing gas passage between a patient and a respirator comprises a pressure gauge connected into the passage which has a pivotal indicator pointer which is movable in response to pressure changes in a direction corresponding to the pressure change, that is, whether it is raised or lowered. An air gate overlies the path of movement of the pointer at both a maximum allowable pressure and at a minimal allowable pressure for the breathing passage. Each of the gates include an air discharge which is interruptable by the pointer when the pressure in the breathing passage reaches the respective maximum or minimum value. In addition, an electronic signal circuit is connected to each gate which includes a logic for actuating a selected signal. The logic circuit for overpressure produced behind the air gauge with a maximum pressure or overpressure has a negation amplifier element, a drop signal and, in common with the logic circuit for the underpressure, a series-switched OR-element, identity element and tuning pipe. The pneumatic logic circuit for underpressure produced behind the minimal pressure air gate has a negation amplifier element, a throttle, a storage connected both ahead and behind the throttle in the circuit, an identity element and a drop signal ahead of the connection to the OR-element. An identity element may be replaced by two series-switched negation elements. The air gate for underpressure has a flow-through lock.

6 Claims, 2 Drawing Figures

MONITOR DEVICE FOR A VENTILATION UNIT

FIELD AND BACKGROUND OF THE INVENTION

This invention relates to control devices in general and, in particular, to a new and useful monitor device for a respirator, in which the inhaled air pressure during inhaling and exhaling is monitored in respect to its duration from a preset value in order to signal elements to respond to any time delayed substandard value.

DESCRIPTION OF THE PRIOR ART

Despite the well-known safe operation of ventilation units or respirators, there is a potential for operational failures, which can have catastrophic consequences for the patient if such failures remain undetected. With artificial ventilation, a pressure rise (stenosis) can be produced by resistances arising in the breathing passage and a pressure drop produced by a leakage in the system. Both pressure changes interfere with breathing gas movements effective between the ventilation unit and the patient.

A monitor device for respirator, equipped with a diaphragm box which is connected to respirator gas feeder lines is known. A one-armed mixing lever which is swivelably supported on a diaphragm box attached bearing bracket, is pushed against the diaphragm by a diaphragm box covering compression-spring load. The mixing lever carries two contacts on its free ends, each of which is interfaced with a timeable contact screw. The contact screws are line-connected to the front contacts of an alarm relay. During respirator operation, the diaphragm is impinged in pulses so that the mixing lever carries out an oscillating motion relative to both contact screws. If the minimal pressure effective between singular gas pulses drops to a value which falls below a contact screw-set value then, an applicable short time contact is closed, which switches in an alarm relay following a specified number of contacts made via a delay unit. If, on exceeding a maximally tolerable gas pressure, a contact is closed between a mixing lever and an interfacing contact screw, then the current circuit of another alarm relay is switched in.

A drawback of this design is that it creates a dependence on electrical auxiliary power and, in conjunction with that, results in a complex design of the unit. In this connection, the fire hazard which exists, e.g., on using oxygen in the ventilation circuit, cannot be ignored, see Swiss Patent No. 461,711.

Another known breathing pressure monitoring unit has a test chamber, wherein two walls facing each other are formed by prestressed diaphragms. This test chamber is connected to the breathing passage between the patient and the ventilation unit by a pressure pipe. One of the switches connected to the diaphragms via moving parts on each breathing cycle alternately switches-in two timer devices. Thereby, on throwing the switch, the applicably not switched-in timer device is reset to its off position.

If, during applicably preset timer switching times, the set pressure within the test chamber is not reached, and/or exceeded on the other switching time, then a signal current circuit is closed, and an alarm is triggered. The switching times, up to the signal, prevent an immediate switching on exceeding and/or falling below the applicably set minimal and/or maximal pressure on alternate breathing phases. An alarm is given only on disturbing the standard flow, be it through leakages in the system or breathing difficulties. On exceeding the maximal chamber pressure set for it, the other switch immediately switches in the signal current circuit via a diaphragm which means that it is independent from the timer devices. This option represents a unique safety measure. This unit also uses electric power and has a complex design, and it includes the disadvantages of the prior art as well, see German Auslegeschrift No. 78,704.

SUMMARY OF THE INVENTION

The present invention provides a monitor device for ventilation units, which is designed in a simple and rugged manner and is operated without electric power. According to the invention, a breathing passage pressure deflected pointer of a pressure gauge is passed through an applicable air gate under a settable, maximal overpressure and/or underpressure, and connected to the air gate, for underpressure via a time function element, there is a pneumatic logic circuit, each ending in signal elements.

The advantages produced by the invention are specifically that, on using oxygen, the use of potentially dangerous electrical components is avoided. Aside from that, pneumatic components are simple and rugged. In addition, the compressed gas required for their operation is always available to the ventilation units an, accordingly, ventilation unit operation is full independent of any further power supply.

In a development of the invention, the pneumatic logic circuit for overpressure produced behind the air gate has a negation-amplifier element, a drop signal, and, in common with the logic circuit for underpressure, a series-switched OR-element, identity element and tuning pipe. The pneumatic logic circuit for underpressure has a post-air gate staged negation-amplifier element, a throttle, a storage, to which a double diaphragm relay is connected, as is also connected ahead of the throttle in the circuit, an identity element, and a drop signal ahead of the connection to the OR-element.

The pneumatic logic circuit for both the overpressure and the underpressure components is developed in conformance with a simple, as well as a safe design. Objective requirements are met in an advantageous manner.

Further developments include, replacing the identity element by two series-switched negation elements, and providing the air gate for the underpressure alarm with a through-flow lock, all of which confirm the simplicity and ruggedness of the design.

Accordingly, it is an object of the invention to provide a monitor device for monitoring the breathing air pressure in a breathing gas passage between a patient and a respirator, which comprises, a pressure gauge connected into the passage which has a pivotal indicator pointer which is movable in response to the pressure changes in the direction corresponding to increase or decrease of pressure, and further includes first and second spaced apart air guages located in the path of movement of the pointer at locations corresponding to a maximum and to a minimum pressure of the breathing passage, each of the gates having an air discharge which is interruptable by the pointer when the pressure in the breathing passage reaches the respective maximum or minimum value and which further includes signal means connected to the gates which are actuated by positioning of the pointer therein.

A further object of the invention is to provide a monitor device for a ventilation unit which is simple in design, rugged in construction and economical to manufacture.

The various features of novelty which characterize the invention are pointed out with particularly in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
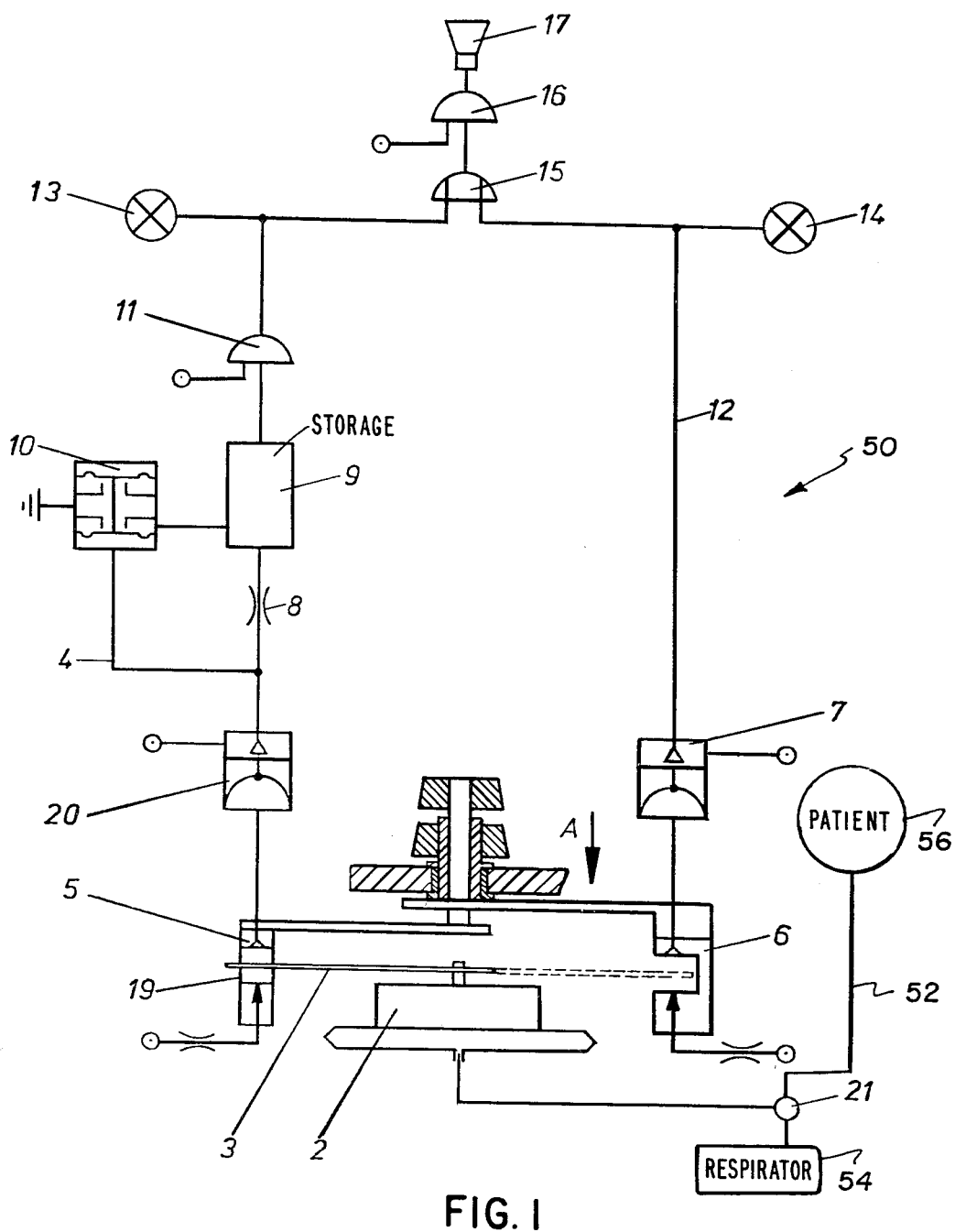
FIG. 1 is a schematic partial sectional view of a monitor device for monitoring the breathing air pressure in a breathing gas passage between a patient and a respirator, constructed in accordance with the invention.
Figure 2:
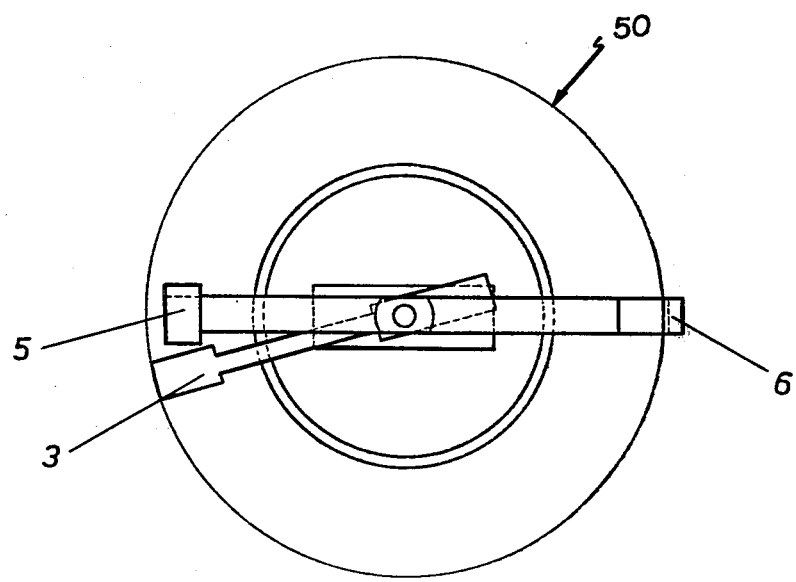
FIG. 2 is a partial plan view, taken in the direction of arrow A of FIG. 1.

Referring to the drawings in particular, the invention embodied therein, comprises a monitoring device, generally designated 50, which includes a pressure gauge 2 which is connected into a respirator breathing passage 52 connected between a respirator 54 and a patient 56. The pressure gauge includes a movable pointer 3 which rotates in accordance with the pressure in passage 52, through a path which will bring it into a gate 6 when there is an overpressure in the breathing passage 52 and into a gate 5 when there is an underpressure in the passage 52. Each of the gates 5 and 6 is provided with means for directing a flow of air through a passage of the gate which is interrupted by pointer 3 upon the occurrence of a maximum or minimal pressure in the passage 52.

Monitor device 50 is interpolated in breathing passage 52, between ventilation unit 54 and a patient 56, via connection 21. The breathing passage pressure is converted to a pressure proportional pointer motion via a mechanical pressure gauge 2, whereby, pointer 3, on entering two air gates 5 and 6, which can be separately set according to their logic value, interrupts a constant air jet. This pulse is processed in pneumatic logic circuits 4 and 12 up to the proper warning signals.

Pointer 3 can pass freely through air gate 6 for the overpressure alarm. Air gate 5 for the underpressure alarm is so developed that, on a drop in the pressure of the breathing passage 52, pointer 3 is moved at first into air gate 5. Upon a further drop in breathing passage pressure, pointer 3 then remains in air gate 5 because of a through-flow lock 19, until the breathing passage pressure again exceeds the set logic value. However, in order that an underpressure alarm is not triggered at each expiration phase, the pneumatic logic circuit 4 contains a storage 9, so that an underpressure alarm is triggered only by a jet interruption exceeding the expiration time.

The operational cases to be watched are both:

(a) Overpressure, e.g., on a stenosis, and (b) Underpressure, e.g., on a leakage in the system.

When there is an overpressure in breathing passage 52, a circuit is closed via logic circuit 12. Pressure gauge 2 is loaded by breathing passage pressure via connector 21, so that pointer 3 is pressure proportionally deflected. Air gate 6 serves as a sensor, which is timed over a specified pressure range. With an undisturbed open air jet at the output of air gate 6, a low pressure signal "1" appears. Post-staged negation amplifier element 7 amplifies the low pressure input signal to standard pressure. The output of negation amplifier element 7 is nulled ("0") by the low pressure signal "1". Signal elements drop signal 14 and tuning pipe 17 are not activated. If the open air jet of air gate 6 is interrupted by pointer 3 at an (alarm) set logic value, then a low pressure signal "0" is applied to negation amplifier element 7. At the output, this then results in standard pressure signal "1". Drop signal 14 for overpressure is activated by signal "1", and a tuning pipe 17 is activated via OR-element 15 and identity 16.

When there is an underpressure in breathing line 52, upon a drop in breathing passage pressure, pointer 3 runs into air gate 5 and interrupts the open air jet. Stopped by through-flow lock 19, pointer 3 remains in air gate 5 even on a further drop in breathing passage pressure. Thus, the open air jet is interrupted for so long as the breathing passage pressure equals or falls short of the set logic value (alarm). During this time, a low pressure signal "0" is applied to post-staged negation amplifier element 20. Thus, the output is switched to standard pressure signal "1". Storage 9 is filled within time t up to standard pressure via fixed throttle 8. The aspirator line of storage 9 on double diaphragm relay 10 is closed by signal "1". On reaching standard pressure in storage 9, identity element 11 is switched through. Thus, drop signal 13 for underpressure and tuning pipe 17 via OR-element 15 and identity 16 are activated. This circuit insures that an "underpressure" warning is triggered only after the passage of sufficient time with the pointer 3 at the gate 5, meaning after the filling of storage 9, which exceeds the standard expiration time. The warning signals for underpressure are continuous signals. If breathing passage pressure exceeds the set alarm value, pointer 3 again releases the open air jet of air gate 5. The output of negation amplifier element 20 is set to "0" by low pressure signal "1", thus, storage 9 exhausts to the atmosphere via double diaphragm relay 10, because its outer chamber is depressurized.

While a specific embodiment of the invention has been shown and described in detail to illustrate the application of the principles of the invention, it will be understood that the invention may be embodied otherwise without departing from such principles.

What is claimed is:

1. In a respiratory device comprising a respirator and breathing gas passage means to connect said respirator to a patient, a monitor device for monitoring the breathing air pressure in said breathing gas passage, said monitor device comprising: a pressure gauge connected into said breathing gas passage and comprising a pivotal indicator pointer which is movable in response to pressure changes in directions corresponding to whether the pressure is raised or lowered, first and second spaced apart air gates located in the path of movement of said pointer at locations corresponding, respectively, to a maximum and to a minimum pressure in the breathing passage, each of said gates having an air discharge which is interruptable by the pointer when the pressure in the breathing passage reaches the respective maximum or minimal value; and signal means comprising a first logic circuit for overpressure connected to said gate located at said maximum pressure location and including a first negation amplifier connected thereto, a first drop signal connected to said negation amplifier to be actuated by output signals therefrom, said signal means further comprising a second logic circuit for underpressure located at said air gate at said minimum pressure location, a series-switched OR-element, both of said underpressure and said overpressure logic circuits being connected to inputs of said OR-element, a first identity element connected to the output of said OR-element, and a tuning pipe connected to said identity element to be actuated by output signals from said OR-element, said second logic circuit including a second negation amplifier element connected to said air gate located at minimum pressure location, a throttle connected to said second negation amplifier, a storage connected both ahead and behind said throttle in said second logic circuit, a second identity element connected to the output of said storage, and a drop signal connected to the output of said second identity element and ahead of the connection to said OR-element.

2. A monitor device, as claimed in claim 1, wherein said identity element comprises by two series-switched negation elements.

3. A monitor device, as claimed in claim 1, wherein said air gate has a through-flow lock.

4. In a respiratory device comprising a respirator and breathing gas passage means to connect said respirator to a patient, a monitor device for monitoring the breathing air pressure, in said breathing gas passage, said monitor device comprising: a pressure gauge connected into said breathing gas passage and comprising a pivotal indicator pointer which is movable in response to pressure changes in directions corresponding to whether the pressure is raised or lowered, first and second spaced apart air gates located in the path of movement of said pointer at first and second locations on the path of movement of said pointer corresponding, respectively, to a maximum and to a minimum pressure in the breathing passage, each of said gates comprising an air discharge path transverse to the path of movement of said pointer to be interruptable by the pointer when the pressure in the breathing passage reaches the respective maximum or minimum value; signal means for signalling the respective pressure when said pointer is in one of said air gates; and circuit means connecting said first and second air gates to said signal means, said circuit means being responsive to the interruption of air pressure in said air gates and comprising storage means connected between said second air gate and said signal means to delay actuation of said signal means in response to minimum pressure in the breathing passage until said pointer has been at said second location for a predetermined length of time.

5. The invention as defined in claim 4, in which said second air gate comprises a through-flow lock to prevent said pointer from moving to a location indicative of pressure below said minimum pressure.

6. The invention as defined in claim 4, comprising: a throttle connected serially between said second air gate and said storage means; and a double diaphragm relay having an input connected between said second air gate and said throttle and having air supply means connected to said storage means to exhaust the pressure in said storage means to atmospheric pressure when said pointer moves away from said minimum pressure location.

* * * * *